United States Patent [19]

Cordner, Jr. et al.

[11] Patent Number: 5,179,983

[45] Date of Patent: Jan. 19, 1993

[54] APPARATUS FOR FILLING MULTIPLE RESERVOIR INFUSION SYSTEMS

[75] Inventors: Edward T. Cordner, Jr., Oceanside; Steven R. Payne; Glenn J. Istratoff, both of San Diego, all of Calif.

[73] Assignee: Block Medical, Inc., Carlsbad, Calif.

[21] Appl. No.: 695,559

[22] Filed: May 3, 1991

[51] Int. Cl.$^5$ .................................... B65B 1/04
[52] U.S. Cl. .............................. 141/27; 141/242; 141/104; 141/105; 604/183; 128/DIG. 1
[58] Field of Search ............... 604/93, 95, 27, 36, 604/39, 43, 125, 181–186, 218, 187, 191, 267; 128/DIG. 1; 141/21, 25, 27, 83, 104, 238, 242, 243

[56] References Cited

U.S. PATENT DOCUMENTS

| | | | |
|---|---|---|---|
| 1,487,414 | 3/1924 | Weatherhead | 141/104 |
| 1,690,067 | 10/1928 | Weeks | 141/242 |
| 2,030,084 | 2/1936 | Winton | 141/242 |
| 2,319,532 | 5/1940 | Codney et al. | 141/242 |
| 2,322,753 | 6/1943 | Thomas | 604/181 X |
| 2,532,560 | 9/1950 | Cozzoli | 141/242 |
| 2,772,705 | 12/1956 | Anderson | 141/242 |
| 2,786,468 | 3/1957 | Singer et al. | 128/DIG. 1 X |
| 3,016,897 | 1/1962 | Kendrick | 604/186 |
| 3,260,286 | 7/1966 | Groves | 141/21 |
| 3,404,713 | 10/1968 | Elford | 141/238 |
| 3,568,735 | 6/1968 | Lancaster | 141/238 |
| 3,720,784 | 9/1966 | Mistarz | 141/238 |
| 3,798,342 | 3/1970 | Sanderson | 141/238 |
| 3,807,131 | 4/1974 | Samson et al. | 141/25 X |
| 3,888,239 | 6/1975 | Rubinstein | 604/191 X |
| 4,168,701 | 9/1979 | Chiulli | 604/181 X |
| 4,226,235 | 10/1980 | Sarnoff et al. | 604/191 X |
| 4,255,096 | 3/1981 | Coker et al. | 417/415 |
| 4,316,558 | 2/1982 | Kubiak | 222/181 |
| 4,434,820 | 3/1984 | Glass | 141/2 |
| 4,501,306 | 2/1985 | Chu et al. | 141/94 |
| 4,563,175 | 1/1986 | LaFond | 604/155 |
| 4,730,648 | 3/1988 | Walter | 141/91 |
| 4,844,298 | 7/1989 | Ohoka et al. | 141/243 X |
| 4,846,797 | 7/1989 | Howson et al. | 604/154 |
| 4,892,518 | 1/1990 | Cupp et al. | 604/93 |
| 4,998,570 | 3/1991 | Strong | 141/21 |
| 5,016,690 | 5/1991 | Ljungerantz | 141/242 |

FOREIGN PATENT DOCUMENTS 3903315 8/1989 Fed. Rep. of Germany ...... 604/191

Primary Examiner—John D. Yasko
Assistant Examiner—Mark O. Polutta
Attorney, Agent, or Firm—Baker, Maxham, Jester & Meador

[57] ABSTRACT

A system for simultaneously filling multiple reservoirs of an IV delivery system comprises a support frame, port positioners on the support frame for positioning a plurality of fill ports of a multiple chamber reservoir, a plurality of injection pumps for injecting a predetermined amount of a fluid, coupling devices for coupling the injection pumps to a fill port of a reservoir, and an actuator for simultaneously coupling the couplers to the fill ports and filling said reservoirs with a predetermined amount of a fluid.

21 Claims, 2 Drawing Sheets

U.S. Patent  Jan. 19, 1993  Sheet 1 of 2  5,179,983
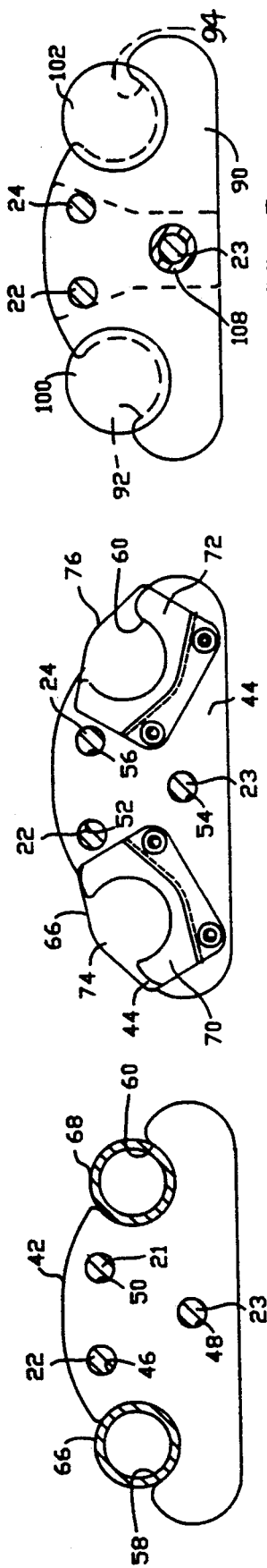
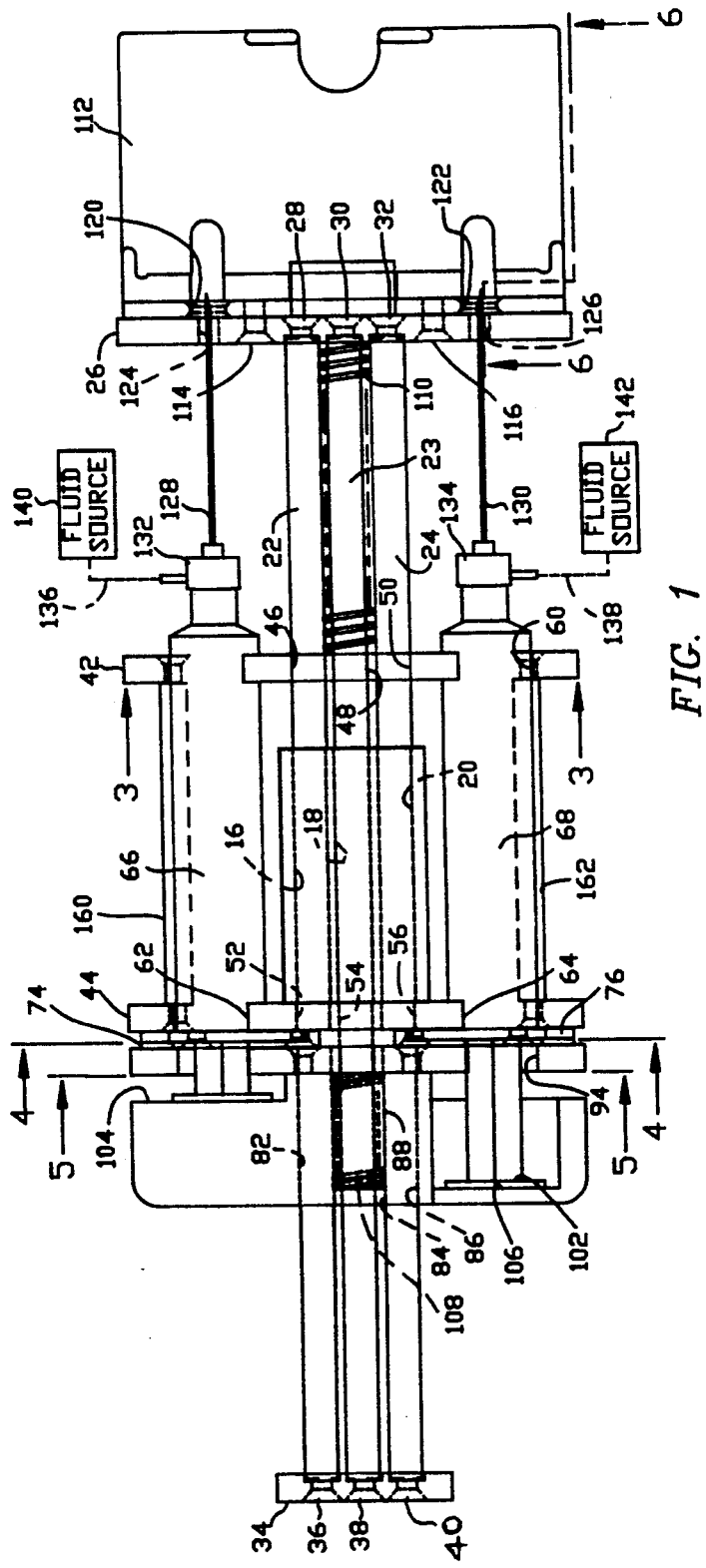
FIG. 5
FIG. 4
FIG. 3
FIG. 1

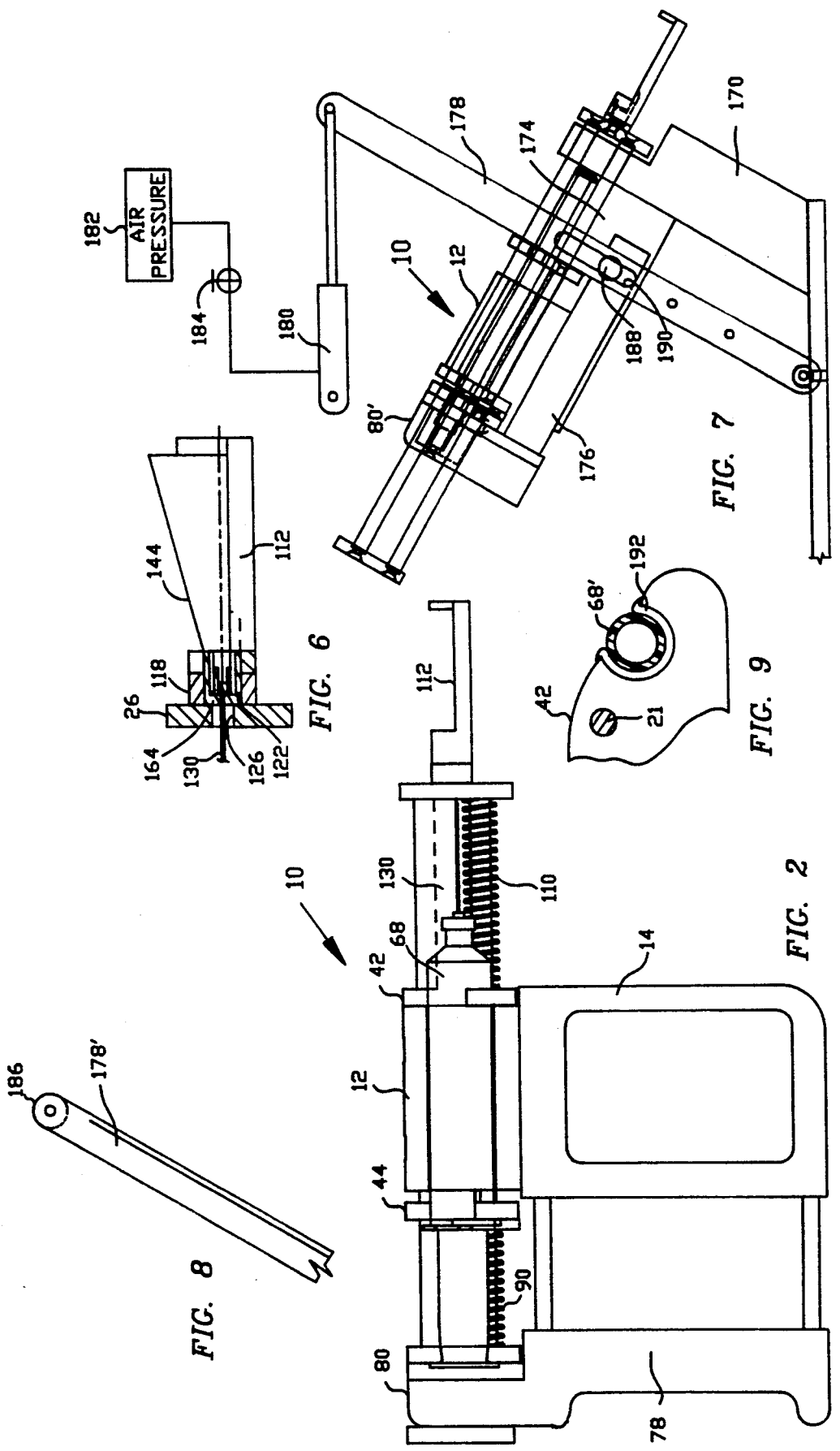

APPARATUS FOR FILLING MULTIPLE RESERVOIR INFUSION SYSTEMS

BACKGROUND OF THE INVENTION

The present invention relates to IV drug delivery apparatus and pertains particularly to an improved apparatus for filling multiple reservoir infusion systems.

Because of the high cost of administering health care in this country, many patients administer their own intravenous therapy (IV) at home. Many times, such therapy requires the periodic infusion of a fluid medication, such as an antibiotic. The patient is usually equipped with an IV site consisting of a catheter connected to the patient by way of a needle installed by trained medical personnel. The catheter is equipped with an injection cap into which a needle is inserted to administer the therapeutic fluid.

Currently, in the health care industry, IV sites are flushed with a saline solution before infusion and after the infusion is complete. This has been carried out in the past by means of a separate syringe and hypodermic needle for each flush. The catheter is then filled with Heparin by means of another syringe after the infusion and second saline flush. This procedure is carried out with at least three syringes, 25G needles with vials of saline and Heparin. The patient or nurse draws fluid into the syringe and pierces the IV sight to inject the fluid for each stage of the procedure. The IV sight is pierced first for saline, second for IV therapy, third for saline and fourth for Heparin. This requires the use and disposal of at least three syringes and four needles with each treatment.

The assignee of the present invention has recently developed a closed system wherein the syringes and multiple needles are eliminated and the sight is pierced only once for each treatment. The fluids for treatment are contained in multiple reservoirs or a reservoir having multiple chambers and connected by a tube to the IV site. The reservoirs are filled by a pharmacist by means of a syringe just prior to use. A fill port is provided for each chamber, and a syringe is used to fill each reservoir with the appropriate amount of fluid.

There is a need for an apparatus for quickly, accurately and safely filling such multiple reservoir system.

SUMMARY AND OBJECTS OF THE INVENTION

It is the primary object of the present invention to provide an improved apparatus for filling multiple reservoir systems.

In accordance with a primary aspect of the present invention, an apparatus for filling a multiple reservoir system comprises means for positioning the fill ports of a plurality of chambers, and means for sequentially coupling and injecting predetermined quantities of solution into the multiple reservoirs.

BRIEF DESCRIPTION OF THE DRAWINGS

The above and other objects and advantages of the present invention will become apparent from the following description when read in conjunction with the accompanying drawings wherein:

FIG. 1 is a top plan view illustrating a preferred embodiment of the invention;

FIG. 2 is a side elevation view of the embodiment of FIG. 1;

FIG. 3 is view in section taken generally on line 3—3 of FIG. 1;

FIG. 4 is a view taken generally on line 4—4 of FIG. 1;

FIG. 5 is a view taken generally on line 5—5 of FIG. 1;

FIG. 6 is a partial detailed view taken on line 6—6 of FIG. 1;

FIG. 7 is a view like FIG. 2 illustrating an alternate modification;

FIG. 8 is a partial detailed view illustrating an alternate modification for actuation; and FIG. 9 is a partial detailed view illustrating an alternate syringe holder.

DETAILED DESCRIPTION OF A PREFERRED EMBODIMENT

Referring to the drawing, and particularly to FIGS. 1 and 2 of the drawings, there is illustrated a preferred embodiment of the present invention. The present invention was devised to provide simple effective and accurate means for quickly and easily filling the fluid reservoirs of an IV flushing system. More specifically, the present invention was designed to provide a means for filling multiple reservoirs of self-contained flushing systems, as disclosed and claimed in co-pending application Ser. No. 07/634,408, filed Dec. 27, 1990 now abandoned, and of common assignment herewith.

Referring particularly to FIGS. 1 and 2, the apparatus comprises a support frame comprising a central generally rectangular block or frame member 12. The support frame member 12 is mounted or attached to a lower rectangular member 14, from which a generally rectangular cutout has been made, essentially forming a handgrip or trigger. The central support frame member 12 is formed with three cylindrical bores 16, 18 and 20 through which elongated cylindrical rods 22, 23 and 24 extend. These bars or rods and the holes through which they extend form a generally triangular pattern.

The member 12 is secured as by clamping to the rods by suitable screws or other suitable means as will be discussed. These rods 22, 23 and 24 are secured at the forward end to a plate 26, such as by means of countersunk screws 28, 30 and 32. They are connected together at the rear end by means of a generally triangular oval shaped plate 34 by means of similar countersunk screws 36, 38 and 40.

A syringe cradle for holding a pair of syringes is formed by a pair of substantially identical shaped generally triangular plates 42 and 44 (FIGS. 3 and 4). These plates each have bores 46, 48, 50, 52, 54 and 56, respectively, which slideably mount them on the rods 20, 22 and 24. Each plate is also provided with a semi-circular cutout 58 and 60 and 62 and 64, respectively, for securely receiving the barrels of a pair of syringes 66 and 68, respectively. The plate 44 is provided with a pair of flanges 70 and 72 and for receiving and capturing the finger flanges 74 and 76 of the syringes. These two plates 42 and 44 are held spaced by a pair of stand off or spacer rods 160 and 162.

As shown in FIGS. 1 and 2, the spacing between plates 42 and 44 is slightly greater than the length of the central frame member 12, thus enabling a slight forward movement of the syringe barrels for coupling the syringes to the injection ports, as will be subsequently explained.

A syringe actuating trigger or hand grip 78 extends downward in alignment with the handgrip 14 (FIG. 2), and has a head portion 80 of a configuration substantially like that of plates 42 and 44. The head 80 includes three bores 82, 84 and 86 slideably mounting it on the three guide rods or bars 16, 18 and 20. A counter bore 88 concentric with the center bore 84 receives a coiled compression spring 108 disposed therebetween and between the plate 44 of the syringe cradle. The head further comprises a plunger retraction plate 90 having bores slideably mounting it on the bars or rods 22, 23 and 24. The retraction plate 90 includes semi-circular cutouts 92 and 94 for receiving the necked down portion of syringe plungers 96 and 98 just forward of the thumb rest or plunger head 100 and 102.

The trigger or actuating head 80 includes a first shallow recess 104 and a second deeper recess 106 for providing a lost motion between actuation of the trigger and engagement of the syringe plunger heads 100 and 102. This is to compensate for different volumes of fluid to be dispensed with each of the respective syringes. For example, the syringe 66 may dispense 10 ml and the syringe 68 dispense 6 ml. This can also be accommodated by different size of syringes, as will be further explained. It can also be compensated by the positioning of or modifying the retraction plate 90 so that one syringe is not retracted as far as the other.

A spring 108 is mounted around the central rod 18 and biases against cradle plate 44 and within recess 88 in the trigger head 80. A similar spring, but of lesser strength 110 is disposed on the rod 22 forward of plate 42 and behind plate 26 biasing them apart. These act as retraction springs.

A support plate or tray 112 of a generally rectangular configuration is secured by way of a pair of screws 114 and 116 to the plate 26, with a spacer and positioner plate 118 disposed therebetween. The positioning plate 118 is provided with a pair of bores 120 and 122 for receiving and positioning fill ports of a flush apparatus reservoir. The fill ports are in the general form of standard injection sites comprising an elastomeric plug in the end of a tube, with a skirt extending over the end of the tube. A needle aligned with the plug may be extended through the plug to communicate with the bore of the tube.

As shown in FIG. 1, these positioning bores are aligned with needle bores 124 and 126 in the plate 26 for receiving or allowing a pair of needles 128 and 130 to extend therethrough, and penetrate fill ports on the reservoirs of a flushing apparatus. The bores 124 and 126 also serve as protectors for the tips of the needles. As shown in FIG. 6, a fill port 164 extends into positioning bore 122 and is penetrated by needle 130 in its forward or connecting position.

The syringes 66 and 68 are equipped with check valve assemblies 132 and 134, with lines 136 and 138 connected to supply reservoirs 140 and 142 for supplying the fluids for injection or for filling the flushing apparatus reservoirs. These check valve assemblies and reservoirs essentially render the syringes' pumps for pumping predetermined amounts of the solutions into reservoirs of a flushing apparatus. As the plunger is withdrawn, a check valve controlling communication with the reservoir opens, a check valve to the needle is closed, and fluid is drawn from the reservoir into the barrel of the syringe. When the plunger is pushed forward, the reservoir check valve closes, and the needle check valve opens and fluid is injected via the needle. A suitable reservoir with tubing and a valve unit for a syringe is available as a McGaw solution transfer set.

In the illustrated embodiment, as shown in FIG. 1, the syringes have been actuated by squeezing the handles or triggers 78 and 14, thus forcing the trigger 78 forward as illustrated, which in turn forces the needles of the syringes forward sufficient to penetrate into fill ports that are positioned in bores 120 and 122, such as a port 64, as illustrated in FIG. 6. Initial actuation of the device by squeezing of the grips 78 and 14 results in the syringes moving forward until plate 44 engages the back surface of central frame member 12, at which time the needles have penetrated into the fill ports of the reservoirs. Thereafter, continued squeezing of the grips results in abutting surfaces 104 and 106 of the actuating handle or trigger 78 in sequence engaging the syringe plunger heads 100 and 102, and upon being squeezed to the limit, injects a predetermined amount of fluid into the respective reservoirs. Thus, common actuating means is provided for performing the combined functions of sequentially coupling said coupling means to said fill ports and actuating said pumps for filling said reservoirs with a predetermined amount of a fluid.

Thus, when the flushing apparatus has been filled, and upon release of the trigger or handle 78, the actuating head 80 will return to its retracted position, as shown in FIG. 2, drawing the plungers of the syringes to their backward position, drawing another charge of fluid from the respective reservoirs 140 and 142 into the barrel of the syringes in readiness for another fill. The flushing apparatus 144 is removed from the support plate 112, and a fresh apparatus is put in its place. Repeating of the actuating steps, as described above, fills the second and succeeding flushing apparatus.

Referring to FIG. 7, a modification is illustrated wherein a power operated unit is provided. In this embodiment, the basic structure or unit 10 is the same, except that one of the actuating members 12 and 80 is mounted to stationary support, and the other is provided with actuating means, such as an air cylinder, or the like.

As illustrated, a unit 10 is mounted on a fixed bracket or stand 170, having an arm 174 by attaching central frame member 12 directly to the arm by any suitable means, such as bolts or screws, not shown. An actuating head 80' is connected by a link 176 to a lever or pair of levers, only one 178 of which is shown, via a pin 188 and slot 190. A power cylinder 180 such as an air cylinder, for example, is provided for actuating the lever 178 for power operation of the filling apparatus. The air cylinder 178 is operated by a source of air 184 controlled by a suitable manual or solenoid valve 186. The cylinder may be double acting for actuating the apparatus in both directions. Alternatively, it may be single acting, as illustrated, with return or retraction being accomplished by springs, as illustrated in FIGS. 1 and 2. It is apparent that the apparatus may be operated by other suitable power means, such as hydraulic or electric motors.

Referring to FIG. 8, a manually operated stationary unit may be provided by modification of levers 178 to become a manual lever 178' with a hand grip 186. These latter two modifications are better suited to assembly line or volume filling of multiple reservoir flushing devices. Other modifications may be made with different types of motors, such as hydraulic or electric utilized for activation of the device. It is also apparent that the actuating head 80, 80' may be fixed to a support, and the central support member 12 moved relative thereto.

A still further modification is illustrated in FIG. 9, wherein a generally C-shaped insert is provided for insertion into the holding slots 60 and 64 of cradle members 42 and 44, FIG. 1, for accommodating a smaller diameter barrel syringe 68'. Thus, the unit may utilize different size syringes, with the same length for a different size charges, such that a full stroke of each syringe is provided to dispense its respective charge of filling fluid. This arrangement is desirable in situations where the dispensed fluid is of sufficient value that wasting of minor amounts thereof is undesirable.

While we have illustrated and described our invention by means of specific embodiments, it should be understood that numerous changes and modifications may be made therein without departing from the spirit and scope of the invention as defined in the appended claims. We further assert and sincerely believe that the above specification contains a written description of the invention and the manner and process of making and using it, in such full, clear, concise, and exact terms as to enable any person skilled in the art to which it pertains, or with which it is most nearly concerned, to make and use the same, and further that it sets forth the best mode contemplated by us for carrying out the invention.

We claim:

1. A system for simultaneously filling multiple reservoirs of an IV delivery system, comprising:
   a support frame;
   means on said support frame for positioning a plurality of fill ports of a multiple chamber reservoir to be filled;
   a plurality of injection pumps mounted on said frame for injecting a predetermined amount of a fluid;
   coupling means for coupling said injection pumps to fill ports of a reservoir positioned on said frame; and
   common actuating means for performing the combined functions of sequentially coupling said coupling means to said fill ports and actuating said pumps for filling said reservoirs with a predetermined amount of a fluid.

2. A filling system according to claim 1 wherein said injection pumps comprise syringes connected through check valve means to a source of fluid.

3. A filling system according to claim 2 wherein said actuating means is operative for actuating said syringes a different amount for injection a different amount of liquid.

4. A filling system according to claim 3 wherein said coupling means comprises an injection needle.

5. A filling system according to claim 4 wherein:
   said positioning means is operative to hold said fill ports at a fixed position; and
   said actuating means moves said syringes for inserting a needle therein into said fill ports.

6. A filling system according to claim 1 wherein:
   said injection pumps comprise a pair of identical syringes; and
   said actuating means forces a plunger of each of said syringes a different amount for injection predetermined different amounts of fluid.

7. A filling system according to claim 1 wherein:
   said injection means comprises a pair of different size syringes; and
   said actuating means forces a plunger of each of said syringes the same amount for injection predetermined different amounts of fluid.

8. A filling system according to claim 6 wherein:
   said actuating means moves said syringes a first predetermined amount for establishing said coupling; and
   said actuating means moves a plunger of each of said syringes a second predetermined amount for said injection.

9. A filling system according to claim 8 wherein:
   said actuating means comprises a carriage for supporting said syringes; and
   means for moving said carriage for establishing said coupling.

10. A filling apparatus for filling multiple chamber IV infusion systems, comprising in combination:
    an elongated support frame;
    means on one end of said support frame for positioning a plurality of fill ports of a multiple chamber reservoir to be filled;
    a plurality of injection pumps mounted on said frame for injecting a predetermined amount of a fluid;
    coupling means for coupling said injection pumps to fill ports of a reservoir positioned on said support frame; and
    common actuating means for performing the combined functions of sequentially coupling said coupling means to said fill ports and actuating said injection pumps for filling said reservoirs with a predetermined amount of a fluid.

11. A filling system according to claim 10 wherein said injection pumps comprise syringes connected through a check valve to a reservoir.

12. A filling system according to claim 11 wherein said actuating means moves said syringes a first predetermined amount for establishing said coupling; and
    said actuating means moves a plunger of each of said syringes for said injecting.

13. A filling system according to claim 12 wherein:
    said injection means comprises a pair of identical syringes; and
    said actuating means forces a plunger of each of said syringes a different amount for injection of different predetermined amounts of fluid.

14. A filling system according to claim 12 wherein said injection means comprises a pair of different size syringes; and
    said actuating means forces a plunger of each of said syringes the same amount for injection of different predetermined amounts of fluid.

15. A filling system according to claim 12 wherein said actuating means comprises manually operated means moveable on said support frame for engaging and forcing a plunger of each of said syringes the same amount for injection of different predetermined amounts of fluid.

16. A filling system according to claim 12 wherein said actuating means comprises power operated means moveable on said support frame for engaging and forcing a plunger of each of said syringes the same amount for injection predetermined different amounts of fluid.

17. A filling apparatus for filling multiple chamber IV site flushing systems, comprising in combination:
    an elongated support frame comprising a central base member and a pair of elongated rails mounted thereto and extending fore and aft thereof;
    a support table fixed on a forward end of said frame for supporting a multiple reservoir infusion apparatus;
    means on said support frame adjacent said support table for positioning a plurality of fill ports of a multiple chamber reservoir of an infusion apparatus;

cradle means for reciprocably mounting a plurality of syringes on said rails of said support frame;

a plurality of syringes mounted on said rails of said support frame;

combined tubing and valve means connected to said syringes for connecting said syringes to a source of fluid for enabling said syringes to act as injection pumps for injecting a predetermined amount of said fluid;

coupling means for coupling each of said syringes to a fill port of a reservoir; and common actuating means for performing the combined functions of sequentially coupling said coupling means to said fill ports and actuating said syringes for filling said reservoirs with a predetermined amount of a fluid.

18. A combination according to claim 17 wherein said coupling means comprises an injection needle; and said actuating means moves said syringes an amount sufficient to insert a needle thereof into said injection ports, and thereafter moves a plunger of each of said syringes a sufficient amount for injection of said predetermined amounts of fluid.

19. A filling system according to claim 18 wherein said actuating means comprises manually operated means moveable on said support frame for engaging and moving a plunger of each of said syringes for injection of fluid.

20. A filling system according to claim 18 wherein said actuating means comprises power operated means moveable on said support frame for engaging and forcing a plunger of each of said syringes for injection of fluid.

21. A filling system according to claim 20 wherein said power operated means comprises an air motor for operation of each of said syringes for injection of fluid.

* * * * *